(12) United States Patent
Romans et al.

(10) Patent No.: US 11,659,995 B2
(45) Date of Patent: *May 30, 2023

(54) SECURE COMMUNICATIONS AND RECORDS HANDLING SYSTEM AND ASSOCIATED METHOD

(71) Applicant: Collaborative Care Diagnostics, LLC, Saint Paul, MN (US)

(72) Inventors: John A. Romans, Saint Paul, MN (US); Paul B. Burke, Hobe Sound, FL (US)

(73) Assignee: COLLABORATIVE CARE DIAGNOSTICS, LLC., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/445,862

(22) Filed: Aug. 25, 2021

(65) Prior Publication Data

US 2021/0378515 A1 Dec. 9, 2021

Related U.S. Application Data

(63) Continuation of application No. 16/484,934, filed as application No. PCT/US2018/019144 on Feb. 22, 2018, now Pat. No. 11,129,533.

(Continued)

(51) Int. Cl.
*A61B 5/00* (2006.01)
*G16H 40/67* (2018.01)
(Continued)

(52) U.S. Cl.
CPC .......... *A61B 5/0022* (2013.01); *G16H 40/67* (2018.01); *H04L 63/08* (2013.01); *H04L 67/125* (2013.01); *H04W 84/12* (2013.01)

(58) Field of Classification Search
CPC ...... A61B 5/0022; G16H 40/67; G16H 50/20; H04L 63/08; H04L 67/125; H04L 65/40; H04W 84/12; H04W 8/24; G06F 21/606
(Continued)

(56) References Cited

U.S. PATENT DOCUMENTS

| 7,166,076 B2 | 1/2007 | Poliac et al. |
| 7,172,555 B2 | 2/2007 | Poliac et al. |

(Continued)

OTHER PUBLICATIONS

"REACH Telemedicine Software Powers the Most Successful Networks" web page; https://reachhealth.com/reach-telemedicine-software/ (Accessed Online May 5, 2017), 2 pages.
(Continued)

*Primary Examiner* — Omar Casillashernandez
(74) *Attorney, Agent, or Firm* — Westman, Champlin & Koehler, P.A.

(57) ABSTRACT

A secure medical device system includes a computer processing device that includes a processor, memory in communication with the processor, an interface enabling communication between the processor and a diagnostic test unit, a first wireless access point, computer-readable instructions stored in the memory and executable by the processor providing a locally-served web site that is browser accessible over the first wireless access point, and a second wireless access point operable concurrently with and independent from the first wireless access point. The locally-served web site is adapted to receive control instructions over the first wireless access point and to generate command signals transmittable over the interface to the diagnostic test unit, and the second wireless access point enables communication between the processor and an external network.

8 Claims, 7 Drawing Sheets

Related U.S. Application Data (60) Provisional application No. 62/463,195, filed on Feb. 24, 2017.

(51) Int. Cl.
*H04L 9/40* (2022.01)
*H04L 67/125* (2022.01)
*H04W 84/12* (2009.01)

(58) Field of Classification Search
USPC .......................................................... 600/300
See application file for complete search history.

(56) References Cited

U.S. PATENT DOCUMENTS

| | | |
|---|---|---|
| 7,214,192 B2 | 5/2007 | Poliac et al. |
| 7,761,261 B2 | 7/2010 | Shmueli et al. |
| 7,983,930 B1 | 7/2011 | Romans |
| 8,229,762 B2 | 7/2012 | Romans |
| 8,688,472 B2 | 4/2014 | Romans |
| 8,706,254 B2 | 4/2014 | Vamos et al. |
| 8,897,198 B2 | 11/2014 | Gaines et al. |
| 8,954,336 B2 | 2/2015 | Blomquist |
| 8,983,378 B2 | 3/2015 | Karuppiah et al. |
| 9,186,518 B2 | 11/2015 | Kothandaraman |
| 9,245,092 B2 | 1/2016 | Romans |
| 9,411,823 B1 | 8/2016 | Rice et al. |
| 9,774,702 B2 | 9/2017 | Carricarte et al. |
| 2005/0055244 A1 | 3/2005 | Mullan et al. |
| 2005/0114170 A1 | 5/2005 | Park et al. |
| 2008/0097913 A1 | 4/2008 | Dicks et al. |
| 2008/0140157 A1 | 6/2008 | Goetz et al. |
| 2009/0157695 A1 | 6/2009 | Roberts |
| 2010/0286488 A1 | 11/2010 | Cohen et al. |
| 2012/0271655 A1* | 10/2012 | Knobel .................. G16H 50/20 705/3 |
| 2013/0054467 A1* | 2/2013 | Dala ..................... G06Q 10/00 705/51 |
| 2013/0160082 A1 | 9/2013 | Miller |
| 2013/0246097 A1 | 9/2013 | Kenney et al. |
| 2013/0269694 A1* | 10/2013 | Patton ................. A61M 15/008 128/203.14 |
| 2014/0129255 A1 | 5/2014 | Woodson et al. |
| 2014/0330584 A1* | 11/2014 | Pillers .................... G06Q 10/10 705/3 |
| 2014/0365654 A1 | 12/2014 | Huerto et al. |
| 2015/0012300 A1* | 1/2015 | Smith ................... G16H 40/20 705/3 |
| 2015/0073498 A1 | 3/2015 | Kothandaraman |
| 2015/0154369 A1 | 6/2015 | Blomquist |
| 2015/0161334 A1 | 6/2015 | Boushka |
| 2016/0078194 A1 | 3/2016 | Romans |
| 2016/0080365 A1 | 3/2016 | Baker et al. |
| 2016/0314262 A1 | 10/2016 | Lauchard et al. |
| 2017/0169176 A1 | 6/2017 | Abiola |
| 2021/0053275 A1* | 2/2021 | Burke ..................... G06F 30/20 |

OTHER PUBLICATIONS

International Search Report and Written Opinion of the International Search Authority dated Jun. 5, 2018, for corresponding International Application PCT/US2018/019144, filed Feb. 22, 2018.

\* cited by examiner

SECURE COMMUNICATIONS AND RECORDS HANDLING SYSTEM AND ASSOCIATED METHOD

CROSS-REFERENCE TO RELATED APPLICATION(S)

This Application is a continuation of U.S. application Ser. No. 16/484,934, which is a § 371 national phase entry of International Application No. PCT/US2018/019144, filed Feb. 22, 2018 and published as WO 2018/156708A1 on Aug. 30, 2018, in English. This application further claims priority to U.S. Provisional Patent Application Ser. No. 62/463,195 filed Feb. 24, 2017. The contents of each priority document is hereby incorporated by reference in its entirety.

FIELD

The present invention relates to secure communication and data management systems and associated methods, and, more particularly, to such systems and methods suitable for use in conjunction with medical testing and monitoring systems and methods.

BACKGROUND

Medical testing, monitoring, diagnosis, and the like can involve a number of different personnel who may be located in different facilities. For example, U.S. Pat. No. 7,983,930 and related U.S. Pat. App. Pub. No. 2016/0078194 disclose a system and method for medical testing that can involve performing a medical protocol on a patient at one location and transmitting patient data to a remote location for diagnosis.

One problem involved in the medical field is the secure transmission and storage of sensitive medical data. Medical devices, such as testing equipment, may still be functional in terms of performing a medical test on a patient, but may not provide for up-to-date security for data transmission and storage. Providing new equipment may be cost prohibitive. Moreover, existing systems may utilize custom hardware that is not readily compatible with other devices, at least not while still meeting suitable security requirements for use in medical applications.

Thus, an alternative communications and records handling system is desired.

SUMMARY

In one aspect, a secure medical device system includes a computer processing device that includes a processor, memory in communication with the processor, an interface enabling communication between the processor and a diagnostic test unit, a first wireless access point, computer-readable instructions stored in the memory and executable by the processor providing a locally-served web site that is browser accessible over the first wireless access point, and a second wireless access point operable concurrently with and independent from the first wireless access point. The locally-served web site is adapted to receive control instructions over the first wireless access point and to generate command signals transmittable over the interface to the diagnostic test unit, and the second wireless access point enables communication between the processor and an external network.

In another aspect, a method for using a medical system includes connecting a first mobile computing device to a computer processing device via a first secure wireless connection, accessing, over the first secure wireless connection, a locally-served web site hosted by the computer processing device via a web browser application on the first mobile computing device, transmitting a control instruction to a diagnostic test unit from the first mobile computing device via the locally-served web site, performing a medical testing operation on a patient with the diagnostic test unit in accordance with the control instruction, and transmitting a first communication record via the locally-served web site from the computer processing device to a cloud-based portal over a second secure wireless connection. The first communication record can contain medical data generated by the diagnostic test unit during the medical testing operation, and the first and second secure wireless connections can be capable of operating concurrently.

In yet another aspect, a medical testing and records handling system includes a mobile computing device configured to execute a web browser application, a diagnostic test unit, a computer processing device that includes a processor, memory in communication with the processor, an interface enabling communication between the processor and the diagnostic test unit, a transceiver, a first wireless access point generated by the transceiver providing a first wireless connection to the mobile computing device over a local wireless transmission range, computer-readable instructions stored in the memory and executable by the processor providing a locally-served web site that is browser accessible over the first wireless access point, and a second wireless access point operable concurrently with and independent from the first wireless access point via the transceiver, a client server, and a cloud-based portal in communication with the computer processing device via the client server. The locally-served web site is adapted to receive control instructions from the browser of the mobile computing device over the first wireless access point and to generate command signals transmittable over the interface to the diagnostic test unit. The second wireless access point links the computer processing device to the client server. The cloud-based portal includes a secure database and serves a portal web site via at least one computer processor, and the at least one computer processor serving the portal web site is located beyond the local wireless transmission range of the transceiver of the computer processing device.

The present summary is provided only by way of example, and not limitation. Other aspects of the present invention will be appreciated in view of the entirety of the present disclosure, including the entire text, claims and accompanying figures.

While the above-identified figures set forth one or more embodiments of the present invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features, steps and/or components not specifically shown in the drawings.

DETAILED DESCRIPTION OF ILLUSTRATIVE EMBODIMENTS

Figure 1A:
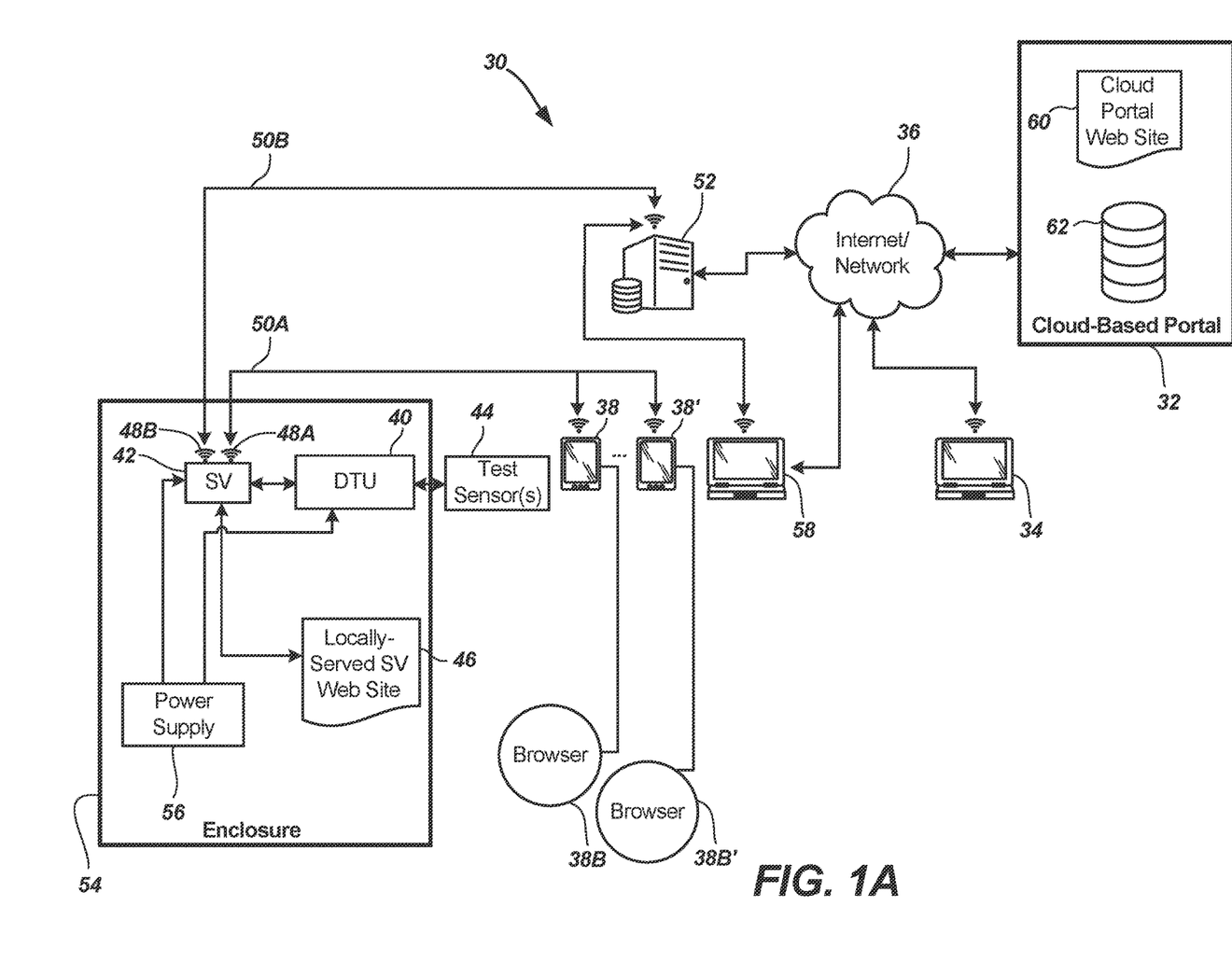
FIGS. 1A and 1B are schematic illustrations of a communication network and testing system according to embodiments of the present invention.

FIG. 1A is a schematic representation of an embodiment of a system 30 that enables secure communications and records management suitable for use in medical testing or other applications. It should be noted that the illustrated embodiment is shown and described merely by way of example and not limitation. As shown in FIG. 1A, the system 30 includes local or on-site components, which can be located at a clinic, hospital, or other location where a patient can be present, as well as components that can be located remotely, including a cloud-based portal 32, and one or more remote computers 34. The local, on-site components can be communicatively linked to the remote components via an external communication network connection 36 such as the Internet.

On-site test device components include a controller 38 that can be in the form of a mobile computing device (e.g., smart phone, tablet, laptop, etc.), wirelessly communicating with a medical device or diagnostic testing unit (DTU) 40 via a security vault (SV) 42. The controller 38 can be a mobile computing device provided by an operator, that is, the mobile computing device need not be a dedicated device for the system 30, but can be a user-supplied device that can be authenticated to communicate with various components of the system 30. In this respect, the operator, or a different operator, can optionally use another controller 38' in the form of a different mobile computing device at another time, as desired. The controllers 38 and 38' need not be identical devices, but in one embodiment are each a device with suitable hardware (e.g., a processor) and memory to run a web browser application 38B (or 38B'), as well as a wireless transceiver such as an IEEE 802.11 (WiFi) or Bluetooth compatible transceiver, output device (e.g., visual display or a disabled-user equivalent, such as a tactile or audio interface), and input device (e.g., touch screen). The web browser application can include functionality for encrypted communication, such as in the form of certificates or keys for secure sockets layer (SSL), transport layer security (TLS), HTTP Secure (HTTPS), and similar encrypted communications. One advantage of the controller 38 (or 38') utilizing a web browser is that a wide variety of mobile computing devices are compatible with the system 30, and users commonly carry such devices in the form of "smart" phones and the like. Web browser applications 38B (or 38B') are commonly already installed on such devices, and provide certain capabilities for secure and encrypted communications that can be utilized in conjunction with the system 30. Moreover, such web browser applications 38B (or 38B') for mobile computing devices can be relatively easily updated to include certificates or other functionality for encrypted communication, thereby maintaining relative up-to-date secure communication capabilities without requiring the system 30 to govern the controller 38 (and 38') or the installation of a specialized application to interact with the system 30. In other words, the controller 38 (or 38') can be maintained largely independently from other components of the system 30, and the system 30 does not need to assume responsibility for updating and maintaining applications on the controller 38 (and 38'). As explained further below, aspects of the system 30 allow the SV 42 to interact with an open-ended set of controllers 38 and 38' while still maintaining secure communications and allowing remote control of the DTU 40.

The DTU 40 is a device that can perform a medical protocol on or with a patient, such as a testing operation, a monitoring operation, or the like. For instance, in one embodiment the DTU 40 can be an oscillometric cardiovascular testing system like those described in U.S. Pat. Nos. 7,166,076, 7,172,555 and 7,214,192. Moreover, in one embodiment, the DTU 40 can include a processor, memory, communication circuitry, air pumps and related valves, power supply (e.g., rechargeable batteries and/or power grid connection), a manifold (e.g., an integrated and monolithic manifold such as a block of a suitable material like aluminum or plexiglass with internal fluid passages/channels machined or otherwise formed to create connections to external components arranged about a perimeter of the block), and related additional circuitry. Providing the manifold as an integrated and monolithic structure allows internal pneumatic components to be closely grouped and less susceptible to thermal and vibrational faults (e.g., reducing risks of hose disconnections). The DTU 40 can connect to external test sensor(s) 44, such as an oscillometric pressure cuff, as discussed further with respect to FIG. 4. It should be noted, however, that a pneumatic/oscillometric device is just one possible embodiment, and the DTU 40 can take other forms in further embodiments. Moreover, in further embodiments additional DTUs can be provided with the system 30.

The SV 42 is a computer processing device with one or more processors, memory, at least one wireless transceiver, and having suitable software and/or firmware. The SV 42 can be implemented, for instance, using a single-board computer device (e.g., a Raspberry Pi® computing device). The SV 42 is connected to the DTU 40 with an interface, such as through an inherently secure direct wired connection (e.g., a universal serial bus (USB) connection). The SV 42 can perform handling and processing of data from the DTU 40, such as initial data scoring and the like. The SV 42 further provides a locally-served web site (or SV web site) 46 and multiple wireless connection points (or hotspots) 48A and 48B. In an alternate embodiment, the SV 42 and the DTU 40 can be integrated, rather than existing as separate sub-systems as shown in FIG. 1A.

At least first and second wireless connection points 48A and 48B are provided concurrently via at least one wireless transceiver of the SV 42, with the first wireless connection point 48A providing a first wireless connection 50A (e.g., using secure WiFi, Bluetooth, or the like) to the controller 38 (or 38'), and the second wireless connection point 48B providing a second wireless connection 50B (e.g., using secure WiFi, Bluetooth, cellular communication, or the like) to the cloud-based portal 32 by way of the network/Internet 36 and a client server 52 and/or a local network (e.g., LAN, WAN). The first and second wireless communication points 48A and 48B can operate separately and substantially independently. All of the wireless connections 50A and 50B can utilize encrypted communications. In this way, the SV 42 acts as an intermediary between the controller 38 (or 38') and the DTU 40, as well as between the DTU 40 (or controller 38 or 38') and the cloud-based portal 32, and can help ensure secure communications and records handling by and within the system 30. Additionally, because an operator using the controller 38 (or 38') will generally be in close physical proximity to the SV 42 and the DTU 40, such as in the same room (e.g., up to an approximately 46 m (150 feet) range of a WiFi connection), the first wireless connection 50A is generally short-range and essentially line-of-sight, making for a highly robust and secure wireless connection. The localized, short-range quality of the first wireless connection 50A, in conjunction with secure or semi-secure physical premises in which the on-site components of the system 30 are located (e.g., building access limitations) can help enhance overall system security, and limiting potential attacks on the first wireless connection 50A. This facilitates use of an open-ended set of controllers 38 or 38' while still promoting security within the system 30. Moreover, the short-range nature of the first wireless connection 50A is relatively immune to interference and downtime, and has relatively low power requirements to be established and maintained.

Communication over the second wireless connection 50B may be non-line-of-sight, and subject to interference (e.g., building construction, electromagnetic interference, etc.). In general, the second wireless connection 50B can extend over a longer distance than the first wireless connection 50A, and the second wireless connection 50B can extend between different rooms or buildings in some embodiments.

The locally-served web site 46 is locally hosted on the SV 42, and includes computer-readable code accessible by the browser 38B or 38B' over the first wireless connection 50A via the first wireless connection point 48A. The locally-served web site 46 can provide a login or authentication protocol for controllers 38 and 38', as explained further below. The login or authentication protocol can be conducted locally by the SV 42, and does not require interaction with the server 52 or the cloud-based portal 32. In some embodiments, the locally-served web site 46 can be access-limited, such that some or all functionality of the locally-served web site 46 (e.g., relating to control of the DTU 40) is accessible only and exclusively via the first wireless connection point 48A and the first wireless connection 50A. In further embodiments, remote control of the DTU 40 is possible through the SV 42 (e.g., using the locally-served web site 46 or other software) to enable telemedicine applications such as a Registered Vascular Technologist (RVT) remotely administering a test on a patient to meet credentialing or certification criteria for reimbursement purposes.

Wireless control of the DTU 40 can occur using the controller 38 or 38' (e.g. tablet, smart phone, etc.). Wireless control is enabled via the browser application 38B (or 38B') on the controller 38 or 38' accessing the locally-served web site 46 rather than a dedicated Smart App (i.e., stand-alone, dedicated software application) to help reduce the burden and expense associated with ongoing maintenance and software updates. Control of the DTU 40 can occur utilizing a user interface provided on the browser 38B or 38B' that interacts and securely communicates with the locally-served web site 46, which in turn communicates with the DTU 40. Because the controller 38 or 38' constitutes an open-ended set of devices that can be independently maintained by operators (i.e., maintained separately from other components in the system 30), there may be operating system and other changes, including the introduction of new operating systems, which make it difficult to maintain compatibility of the system 30 with such controllers 38 and 38' without extensive ongoing updates to a dedicated software application to maintain compatibility (and security). Furthermore, the system 30 lessens hardware demands on the controller 38 or 38', allowing nearly any mobile computing device capable of running a suitable web browser application 38B or 38B' to be used to control the DTU 40 via the SV 42. This is accomplished, in part, through hardware load sharing by the SV 42 and the controller 38 or 38', with the SV 42 taking on tasks via the locally-served web site 46 that would otherwise increase hardware requirements on the controller 38 or 38', and vice-versa. For instance, the DTU 40 and SV 42 can each be provided without a display, keyboard, mouse, or the like.

Because the locally-served web site 46 does not depend on the network/Internet connection 36, the status of the second wireless internet connection 50B is not critical to performing a medical protocol on a patient using the DTU 40. If a connection to the network/Internet 36 is lost (e.g., by server 52), or communication with the cloud-based portal 32 is otherwise lost or interrupted, the locally-served SV web site 46 and the first wireless connection 50A still allow for communication between the controller 38 (or 38') and the SV 42 to control the DTU 40 via the first wireless connection point 48A. Data communications between the SV 42 and the cloud-based portal 32 can be queued (e.g., at or within the SV 42) until the connection over the network/Internet 36 is restored.

In the embodiment illustrated in FIG. 1A, the DTU 40 and the SV 42 can be commonly positioned with an enclosure 54. The enclosure 54 can allow the DTU 40 and SV 42 to be in an integrated package that is seamless for user purposes, and to provide a single mounting point for the DTU 40 and SV 42 (e.g., with a single mounting bracket or other mechanical attachment structure). Furthermore, a power supply 56 can be provided at least partially within the enclosure 54 for one or both the DTU 40 and the SV 42. The power supply 56 can be a battery (e.g., rechargeable battery), to allow for mobile operation and/or continued operation in the event of loss of a primary power supply (e.g., grid power). The power supply 56 can be external to the enclosure 54 or omitted in further embodiments.

The server 52 can be a local, on-site device connected to the SV 42 via the second wireless connection 50B and the second wireless connection point 48B. The server 52 can be or include a network router or switch, and can optionally include a local medical records system and/or database, such as part of an Electronic Medical Record (EMR) and/or Practice Management (PM) system accessible from one or more computer terminals 58. The server 52 can provide a pass-through Internet connection to the controller 38 or 38' via the SV 42 and the first and second wireless connections 50A and 50B, or via an additional, separate wireless connection. In embodiments in which the enclosure 54 is used in a portable manner, the server 52 may not be in close proximity and the second wireless connection 50B may not be active. However, when the enclosure 54 is later brought into proximity to the server 52 the second wireless connection 50B can be restored or otherwise activated. Additionally, in further embodiments, the second wireless connection 50B could be replaced with or supplemented by a wired network connection, as desired.

The cloud-based portal 32 can be located remotely from the controller 38 or 38', the DTU 40, the SV 42 and the server 52, and can include a cloud portal web site 60 and a secure database 62. The cloud portal web site 60 can be served using one or more servers each having one or more computer processors and suitable memory, based on computer-readable programs code. In some embodiments, the cloud portal website 60 can be served with hardware located beyond a local wireless transmission range of the second wireless access point 48B and the second wireless connection 50B. The database 62 can be a discrete database or a distributed database, and can be secured using suitable security protocols (e.g., with encryption, etc.).

During operation, medical data (e.g., test data) from the DTU 40 or other sources is sent via the SV 42 to the cloud-based portal 32. Such transmission can happen automatically, such as on an event basis upon completion of a medical protocol or on a periodic schedule. All medical data produced by the DTU 40, the controller 38 or 38' and/or the SV 42 can be sent or conveyed to the cloud-based portal 32 and stored in the secure database 62. In this way, medical data need not be stored on the DTU 40, the controller 38 or 38' or the SV 42, and, indeed, can be explicitly purged from the DTU 40, the controller 38 or 38' and/or the SV 42 upon transmission to the cloud-based portal 32. Such deleted and purging of data helps minimize data breach risks and enhances the security of the system 30. As already noted, if a connection to the network/Internet 36 is lost or interrupted, data communications between the SV 42 and the cloud-based portal 32 can be queued through temporary storage at or within the SV 42 until the connection to the cloud-based portal 32 over the network/Internet 36 is restored.

Cloud-based data analytics and scoring allows medical data in the database 62 to be analyzed and initial, automated determinations made prior to analysis by a qualified medical professional. A diagnosis or other analysis by a qualified medical professional can then be made based on data from the could-based portal, such as in a manner described in commonly-assigned U.S. Pat. App. Pub. No. 2016/0078194, for instance.

The cloud-based portal 32 does not need to authenticate individual controllers 38 or 38'. However, the cloud-based portal 32 can authenticate the SV 42, and can perform administrative regulation of the SV 42 in some embodiments.

Furthermore, in some embodiments the cloud-based portal 32 can coordinate scheduling of testing and other procedures involving the DTU 40 and/or involving other devices, such as DTUs at other test locations and/or providing other test modalities (peripheral neuropathy diagnostics, cardiovascular diagnostics, spirometry diagnostics, etc.). Such scheduling can follow HL-7 communication protocols, or other suitable protocols. Additionally, in some embodiments the cloud-based portal 32 can bundle multiple studies performed with the DTU 40, or gathered from other testing modalities or sources, into a single encounter. The bundled data (e.g., peripheral neuropathy diagnostic data, cardiovascular diagnostic data, spirometry diagnostic data, patient identification data) can then be sent to an EMR system, disease management software, and the like, such as using HL-7 communication protocols or other suitable communication protocols. Such functionality allows the web-based portal to act as a centralized hub for communication with a variety of different devices and systems while reducing or minimizing the need for users to undertake multiple encounters with one or more systems to gather test and patient data from multiple studies and/or test modalities.

Figure 1B:
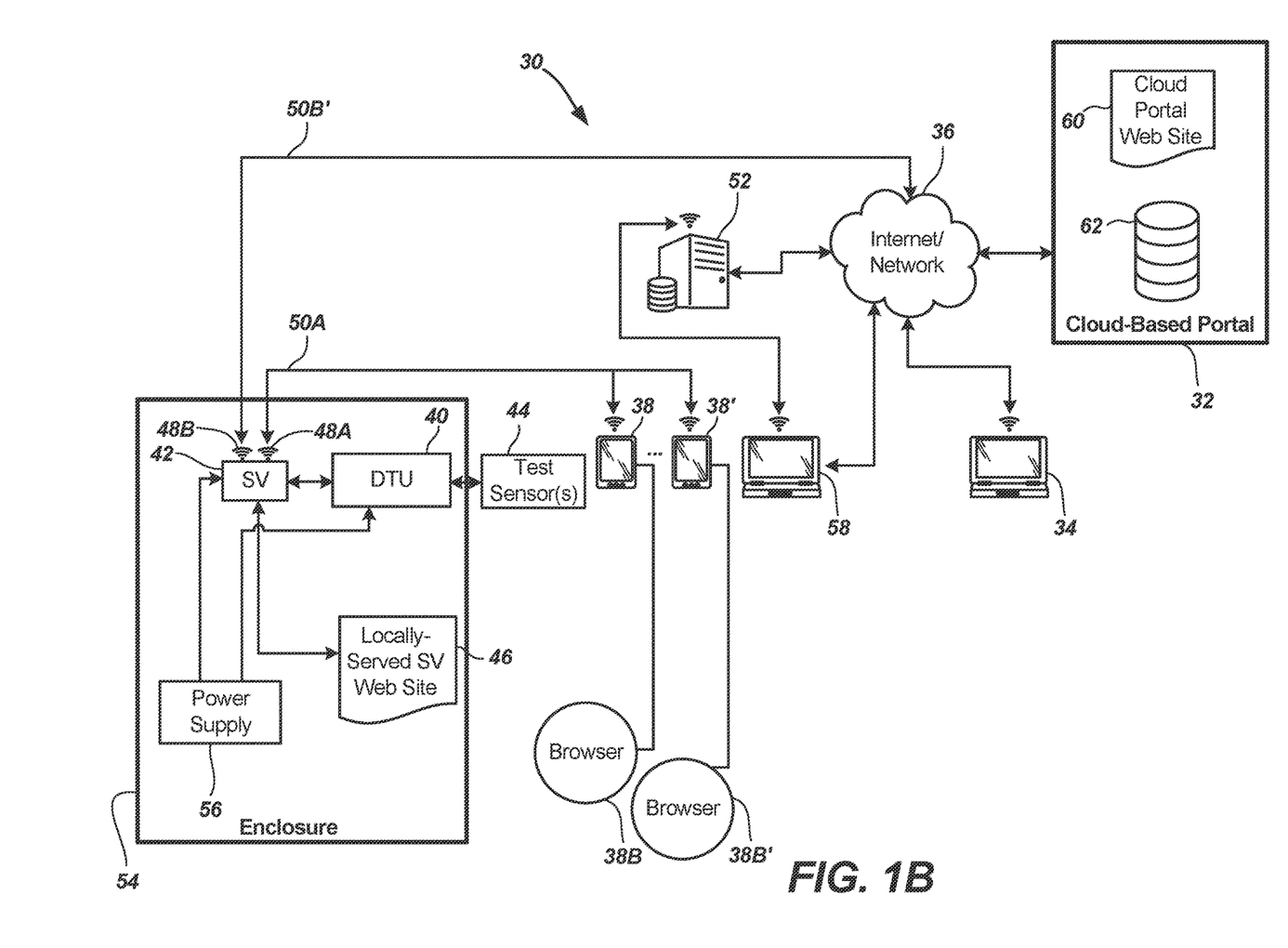

FIG. 1B illustrates an alternative embodiment of the system 30 in which a second wireless access connection 50B' is provided as a cellulation communication link between the second wireless access point 48B (e.g., a cellular modem) and the Internet/network 36. The server 52 can be omitted in further embodiments, or can remain to communicate indirectly with the SV 42 via the Internet network 36.

Figure 2:
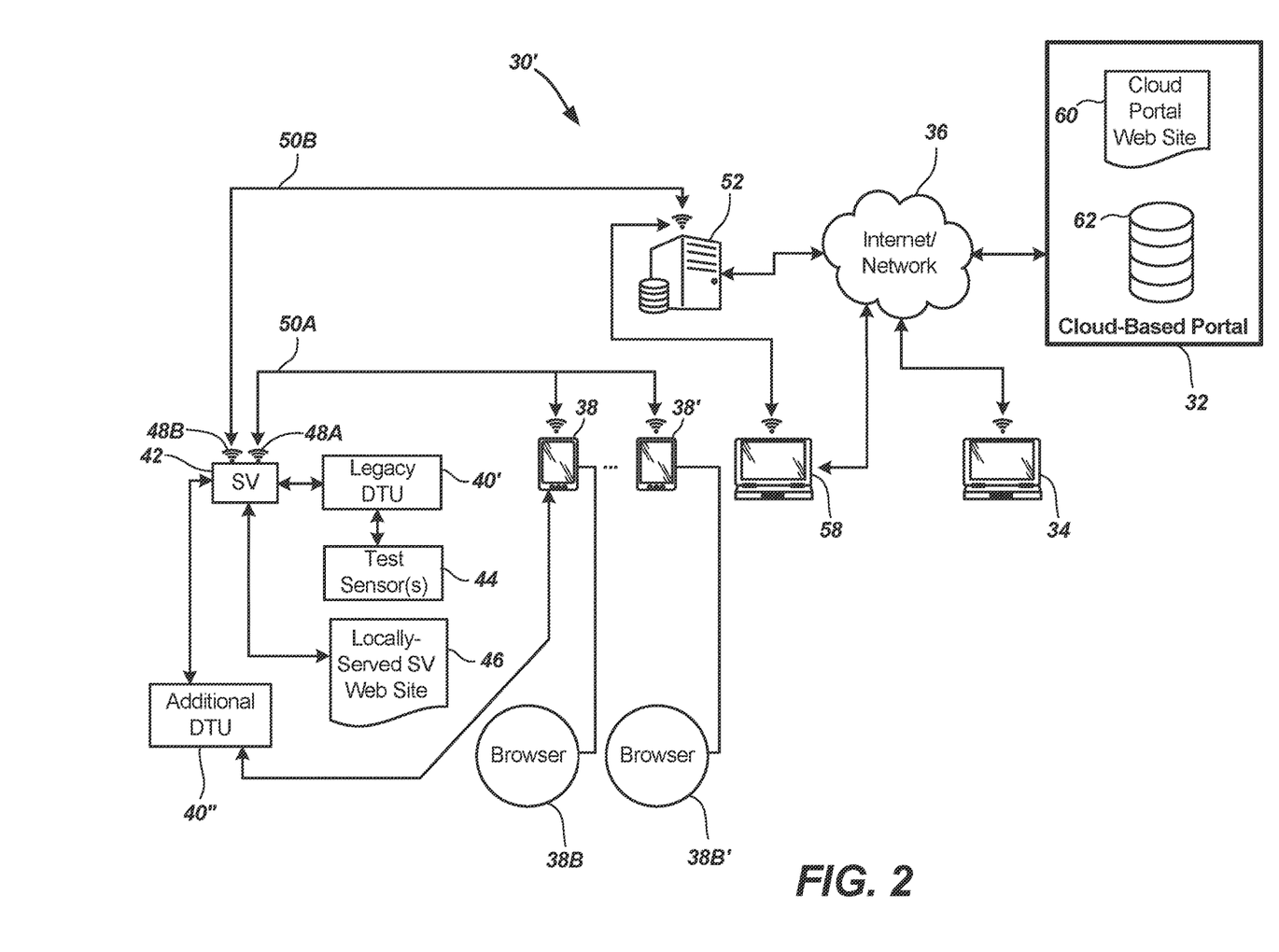
FIG. 2 is a schematic illustration of a communication network and testing system according to a retro-fit embodiment of the present invention.

FIG. 2 is a schematic illustration of another embodiment of a system 30' that provides backwards compatibility. In general, the system 30' is similar to the system 30 described above. However, one or more legacy/existing DTUs 40' can be coupled to the SV 42 to upgrade security and communications functionality seamlessly. The SV 42 can have its own dedicated housing separate from the DTU 40'. Upgraded SV components can be provided as a retrofit kit. As shown in FIG. 2, an additional DTU 40" is also connected to the SV 42 and/or the controller 38 (or 38').

The system 30 or 30' can facilitate controlling and gathering data from multiple DTUs 40', 40" supporting multiple, different test modalities. In other words, the SV 42 can be utilized with a variety of DTUs 40', 40", including legacy equipment, allowing various DTUs 40', 40" to be utilized in a secure data communication environment even if those DTUs 40', 40" have old or insufficient security capabilities of their own. Moreover, multiple DTUs 40, 40' and 40" of nearly any configuration can be utilized concurrently with the SV 42, as explained further below. For instance, in one embodiment, the additional DTU 40" can comprise a device that attaches directly to the controller 38, such as by a USB connection, and is directly controlled by the controller 38, which in turn communicates with the SV 42 over the first wireless connection 50A to transmit data from the DTU 40". Although FIG. 2 depicts DTU 40" connected to both the SV 42 and the controller 38, the DTU 40" can be connected to only the SV 42 or the controller 38 in some embodiments.

Figure 3:
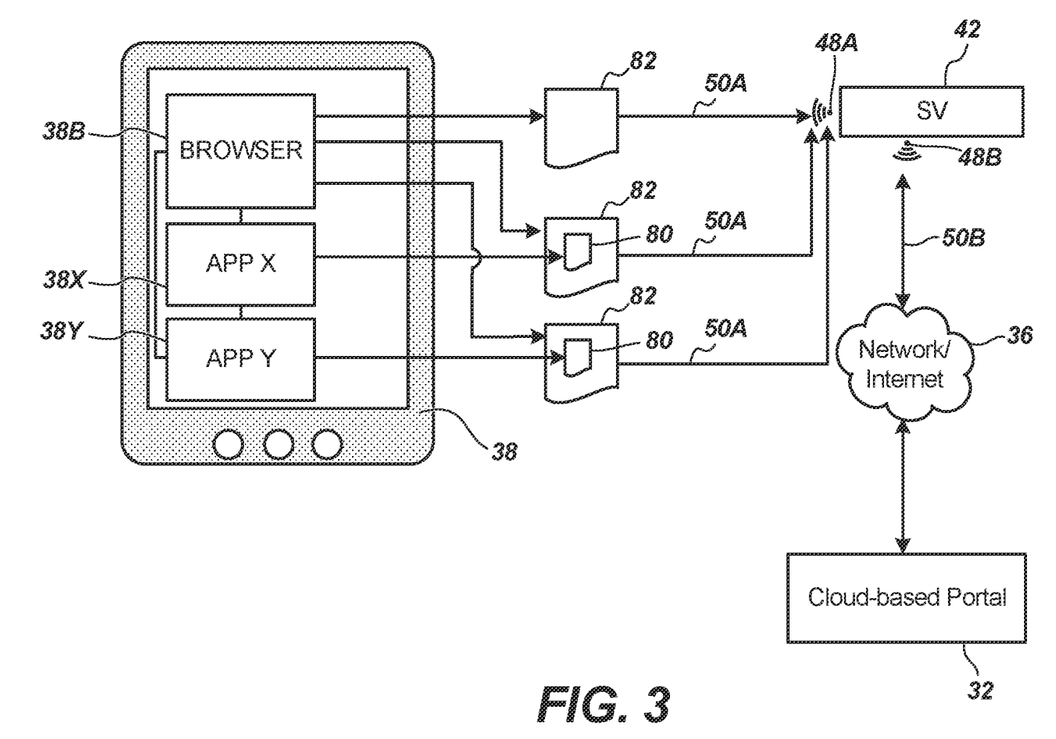
FIG. 3 is a schematic diagram of an embodiment of a secure data handling sub-system according to the present invention.

FIG. 3 is a schematic diagram of an embodiment of a secure data handling sub-system of the system 30 or 30'. As illustrated in the embodiment of FIG. 3, data encapsulation is provided by encapsulating data 80 (e.g., test reports, images, and the like) from nearly any DTU 40, 40' or 40" (see FIGS. 1A, 1B, and 2) in or with a communication record 82 that can be transmitted to and handled by the cloud-based portal 32. The data 80 can comprise a file or other data set associated with dedicated applications 38X and 38Y accessible from the controller 38, or otherwise accessible from the browser 38B running on the controller 38 in communication with the locally-served web site 46. The encapsulation can involve embedding or attaching the data 80 to or with the communication record 82 at either the controller 38 or the SV 42, and allows for secure integration of various DTUs 40, 40' or 40" and associated files in native format(s) with electronic medical records systems (e.g., running via the server 52) and for centralized communications without the need for individualized software interfaces to be programmed. The communication record 82 can include a header or other identifying information that is recognizable by the cloud-based portal 32 in a portal format. It is possible for each data package 80 generated by different DTUs 40, 40' or 40" and/or applications on the controller 38 to be encapsulated in or with a different communication records 82, as illustrated, or, in alternate embodiments, for one or more data packages 80 to be encapsulated in or with a common communication record, or a combination of those approaches can be utilized. In this way, data generated by the DTU 40 in a cloud portal format can be transmitted in one communication record 82, while data 80 generated by the additional DTU 40' in a different, native DTU format can be encapsulated in another communication record 82, with both records 82 transmitted to the cloud-based portal 32 for handling, for instance.

A reduction of data entry is facilitated by the data encapsulation in or with the communication record 82. This reduces the demands on the controller 38, which may lack a keyboard or mouse, making data entry with the controller 38 more time consuming and error-prone. Minimal patient data can be entered, such as a patient ID and/or name, using the controller 38. Associated test data 80 can then be concatenated or otherwise fused with more extensive patient data at or via the cloud-based portal 32. This reduces the need for redundant data entry when multiple test modalities are deployed for a given patient. Moreover, automated population of data fields can be achieved, as desired.

Figure 4:
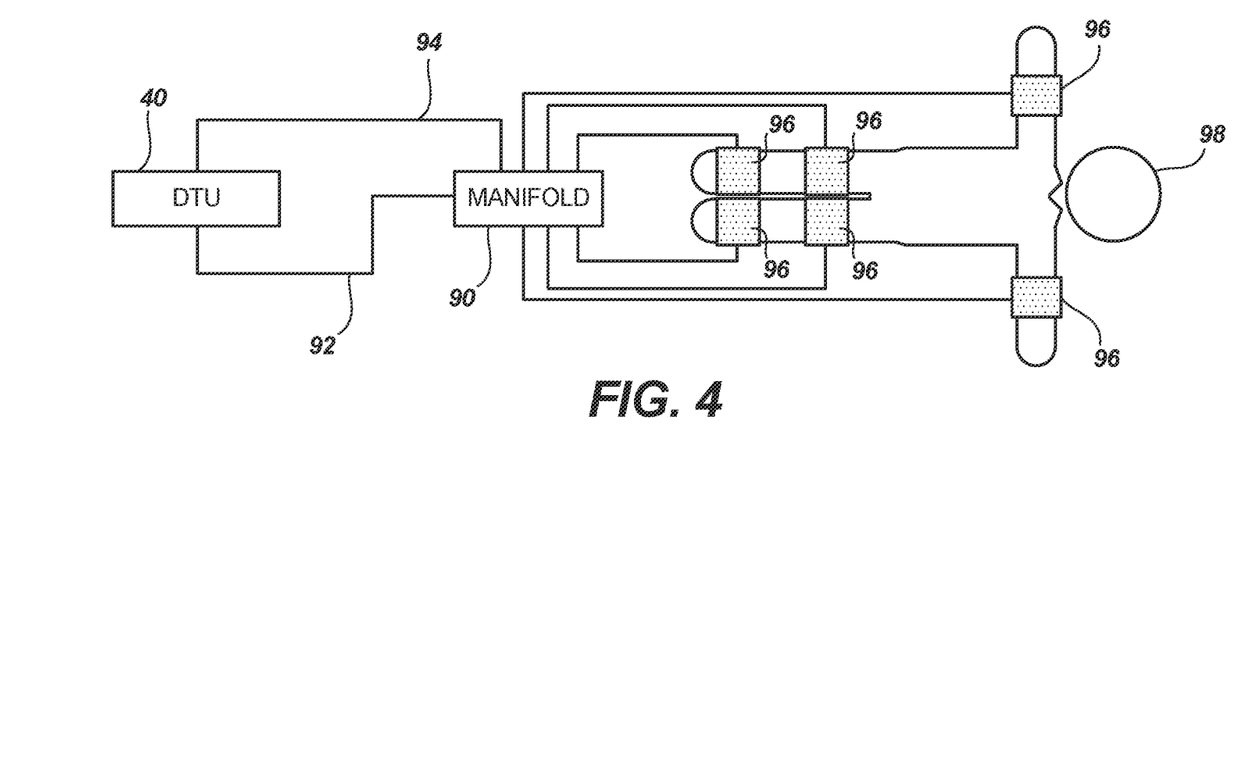
FIG. 4 is a schematic plan view of an embodiment of a medical testing sub-system with a manifold according to the present invention.

FIG. 4 is a schematic plan view of an embodiment of a medical testing sub-system of the system 30 or 30'. In the illustrated embodiment, the DTU 40 is configured to provide oscillometric cardiovascular testing, such as to perform an ankle-brachial index (ABI) test and/or to perform other tests to gather data for diagnosis of peripheral arterial disease (PAD). The DTU 40 is connected to a manifold 90 by at least one pneumatic hose 92 (preferably a single hose) and at least one signal wire 94. The DTU 40 can generate pneumatic pressure and control commands, and the manifold 90 can include controllable valves to selectively deliver and sense pneumatic pressure at one or more pressure cuffs 96 positioned on a patient 98, such as at a toe, ankle, calf, thigh and arm (bicep). During operation, software controlling the DTU 40 provides commands to the manifold 90 which in turn electronically controls valves determining which air hoses and attached blood pressure cuffs 96 are to be included in the pneumatic circuit at any given time. This allows for the system 30 to perform a test on a single patient segment, a series of segments (performed sequentially), or several segments simultaneously. It should be noted that the embodiment of the testing sub-system shown in FIG. 4 is illustrated and described merely by way of example and not limitation. As already noted, other testing modalities are possible in further embodiments.

Figure 5:
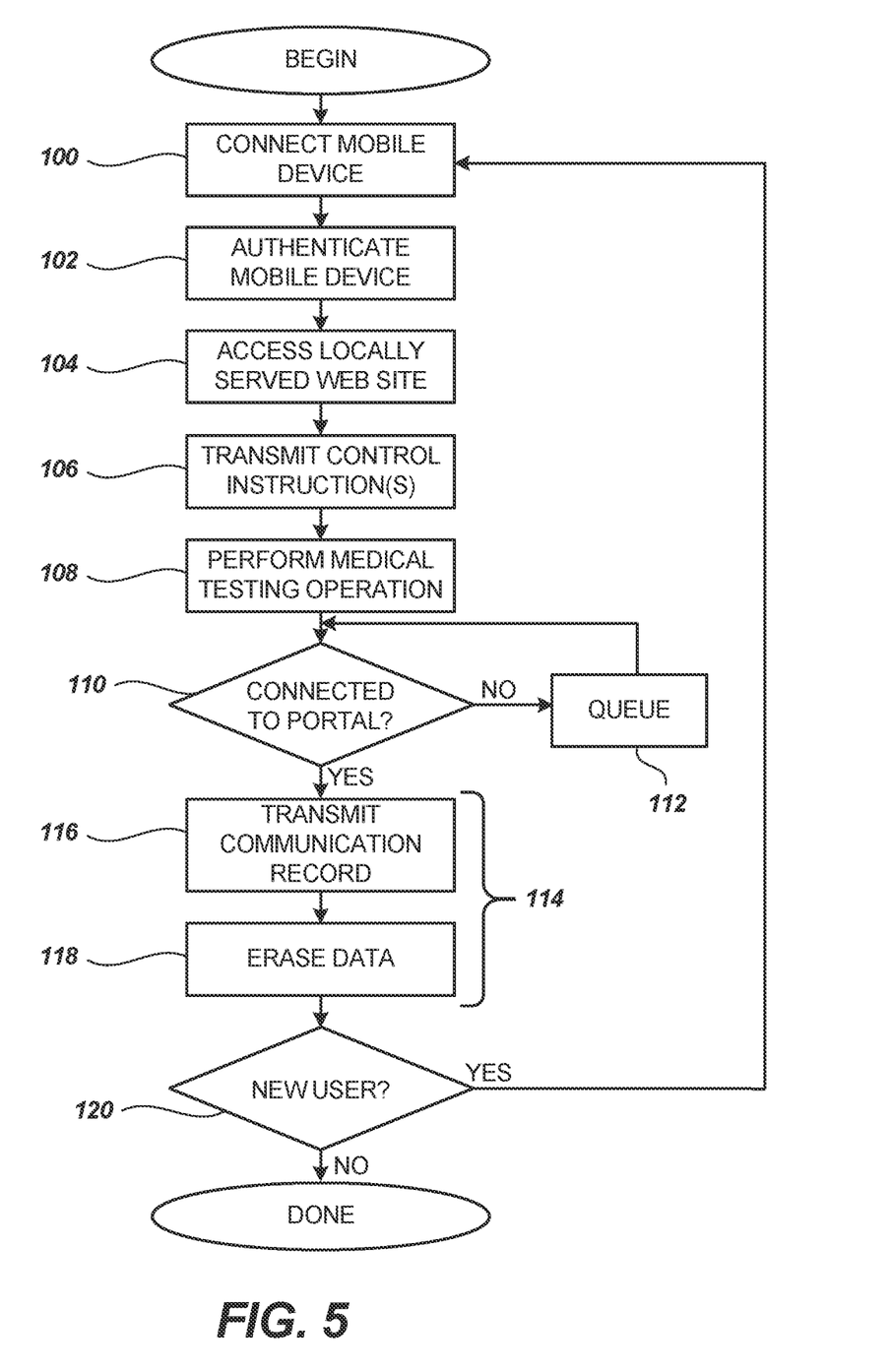
FIG. 5 is a flow chart of one embodiment of a method of secure communication and record handling according to the present invention.

FIG. 5 is a flow chart of one embodiment of a method of secure communication and record handling, which can be used with the system 30 or 30'. Although not explicitly shown in FIG. 5, the method can include providing some or all of the components of the system 30 or 30' described above. It is noted that various steps of the method disclosed herein can be performed using computer-readable instructions that can be saved in memory and executed using one or more processors, as will be understood by persons of ordinary skill in the art.

Initially, a user or operator, who can be a medical technician, nurse, doctor or the like, connects a mobile computing device (or other suitable controller) 38 to the first wireless access point 48A of the SV 42 (step 100). An authentication or login protocol is then performed to authenticate the mobile computing device 38 (step 102). If authentication is successful, the first wireless connection 50A is fully established and the mobile computing device 38 is granted access to functionality of the locally-served web site 46 by the SV 42 by way of a browser application 38B launched and run on the mobile computing device 38 (step 104). It is not necessary that the mobile computing device 38 have an Internet connection to achieve access through the SV 42 in this manner, just that the mobile computing device 38 can wirelessly connect to the first wireless access point 48A. If authentication is unsuccessful, such as because the user lacks authorization or current login credentials, then access to the locally-served web site 46 is denied by the SV 42, and the user can be blocked from performing any remaining steps of the method (e.g., by being denied control of the DTU 40). User credentials and network access can be managed by authorized administrative personnel via the cloud portal website 60 (e.g., over the second wireless connection 50B by administrative personnel located remotely from the DTU 40 and/or SV 42 using computer 34 or 58).

After gaining access at step 104, the mobile computing device 38 can be paired with a target DTU 40, and the user can initiate a medical protocol from the mobile device 38, via the web browser application 38B. As part of such a medical protocol, a user interface provided via the browser application 38B on the mobile computing device 38 can enable a limited amount of data to be entered so that the user can create a patient record or select one from a list of scheduled patient studies, for example. In one embodiment, the browser-based user interface accessed via the mobile computing device 38 (and the browser 38B) then allows the user to control the DTU 40 and transmit one or more control instructions in the form of one or more signals transmitted over the first wireless connection 50A, preferably in an encrypted format, that are received by the SV 42 via the locally-served web site 46 and used to control operation of the DTU 40 (step 106). The user can then perform a medical testing operation or study (or other medical protocol) on a patient using the DTU 40 as controlled via the mobile computer device 38 and the browser application 38B (step 108). The user can control the administration of a patient medical study by commanding a processor embedded the target DTU 40 to perform specific medical studies. For example, if the DTU 40 comprises an oscillometric testing system of the type described above with respect to FIG. 4, the medical testing operation can be an ABI test. As elements of the patient study are completed, the results will be stored on the target DTU 40 (e.g., in suitable local DTU memory) and/or on the user's mobile computing device 38.

Control instructions transmitted at step 106 can also relate to processing test results, administrative and non-medical actions, and to the handling of previously-obtained medical records or data, including data and records obtained from sources other than the DTU 40 (e.g., from the additional DTU 40'). For example, the user can select certain cardiovascular test results including pulse volume recording (PVR) waveform segments, PVR amplitude and gain calculations, return of blood flow when using a photoplethysmography (PPG) probe as a sensor for blood pressures, as well as executing suitable "Save", "Clear", "Next", "Exit" and other conventional data handling and user interface functions. Such actions can include control of encapsulation of medical data 80 from other applications 38X and/or 38Y running on the mobile computing device 38. Moreover, the user can transmit control instructions from the mobile computing device 38 and browser 38B that relate to interaction with the cloud-based portal 32. Additionally, the system 30 can include the ability to remotely control (e.g., via the cloud-based portal 32) the user's mobile computing device 38 (e.g., by controller the browser application 38B) so that a credentialed individual could perform a medical diagnostic procedure if the operator was not sufficiently credentialed. A virtual private network (VPN) or other suitable mechanism can be utilized to remotely control the browser 38B and/or entire mobile computing device 38 in some embodiments.

Test or other medical data (including, for example, "in test" calculated values) generated based on control instructions from the user can then be transmitted to the cloud-based portal 32, via the network/Internet 36. For instance, once a given study has been completed, electronic data indicative of one or more aspects of the study can be sent from the embedded hardware of the DTU 40 (and/or the mobile computing device 38) to the cloud-based portal 32, which can happen on an automated basis, such as using a synchronization protocol that does not require affirmative action by the operator. First, the SV 42 can check to see if a connection to the cloud-based portal 32 is active (step 110). If the connection to the cloud-based portal 32 is inactive, then the data can be queued at the SV 42 (step 112), and the method can return to step 110 to check to see if a connection to the cloud-based portal 32 has been established, restored, or reactivated. In some embodiments, a notice or alert regarding the queueing status can also be generated. If a connection to the cloud-based portal 42 is active, a synchronization protocol can be performed (step 114). The synchronization protocol can include transmitting at least one communication record 82 from the SV 42 to the cloud-based portal 32 (step 116) and erasing or purging the transmitted data from at least the mobile computing device 38 (step 118). The erasing step can include clearing cache(s) of the web browser application 38B as well as clearing the transmitted data from embedded hardware (e.g., the processor(s)) and memory of the mobile computing device 38, and can further include erasing the transmitted data from embedded hardware and memory of the SV 42 and/or the DTU 40. Local erasure can be performed concurrently with the transmission step 116, or on a separate protocol or schedule. In one embodiment, local patient data is automatically erased upon or after transmission to the cloud-based portal. This erasure promotes security, and helps reduce risks associated with having sensitive data on local devices, such as the highly-portable mobile computing device 38.

The data received at the cloud-based portal 32 can be processed in any desired manner, and can be subjected to a diagnosis by a qualified medical specialist. For instance, once studies have been successfully uploaded to the cloud-based portal 32, they can be interpreted by a suitable medical specialist who is in communication with the cloud-based portal through a remote computer (e.g., computer 34). The completed study, including specialist interpretation and/or diagnosis, can then be made available for export to a client-designated (e.g., user-designated) EMR system. There can be multiple EMR systems that connect to the cloud-based portal 32 for study export, because the primary care physician (e.g., operator) and diagnostic specialist may both want to have the final study stored in their respective EMRs. These export functions can be handled by the could-based portal, which reduces hardware and other demands on the SV 42, mobile computing device 38, and other on-site equipment. Other administrative and formatting of the data can also occur at the cloud-based portal 32, such as converting the data into a results presentation format equivalent to that generated from legacy devices, and can be retained in the secure database 62 for archival access by users for a pre-determined amount of time. Moreover, claims or billing information on completed studies can be sent from the cloud-based portal 32 to one or more separate third-party processors for claims or billing processing. Third-party processors can submit a report back to the cloud-based portal 32 on the status of the submitted claims or bills.

The mobile computing device 38 can then disconnect from the SV 42, terminating the first wireless connection 50A. At any time thereafter, or alternatively while the device 38 remains connected, a new user can seek access (step 120). The new user can then perform step 100 utilizing the additional mobile computing device 38'. It should be noted that in this context the new user could be a different user utilizing the same mobile computing device 38 and providing different login credentials, or could be the prior user simply initiating a new user session with any mobile computing device 38 or 38'.

The steps shown in FIG. 5 and described above are disclosed merely by way of example and not limitation. Additional steps not specifically illustrated in FIG. 5 can also be performed, and certain steps may be omitted in alternative embodiments. For example, other steps for using the system 30 can include the following. Scheduling functionality can be provided to manage medical studies performed with the DTU 40. For instance, a user can schedule a patient for a study (e.g., ABI and/or other medical test(s)) with the user interface of the cloud portal web site 60 or via an HL-7 inbound interface with EMR or PM software. As another example, each DTU 40 or 40' can be configured with an onboard processor that can wirelessly connect to a local network (e.g., via the server 52). When a given DTU 40 or 40' is turned on, the DTU 40 or 40' can register (e.g., automatically) with the cloud-based portal 32 to confirm that the DTU 40 or 40' is available for testing. Such registration can be used for scheduling purposes, via the cloud-based portal 32, for instance.

Figure 6:
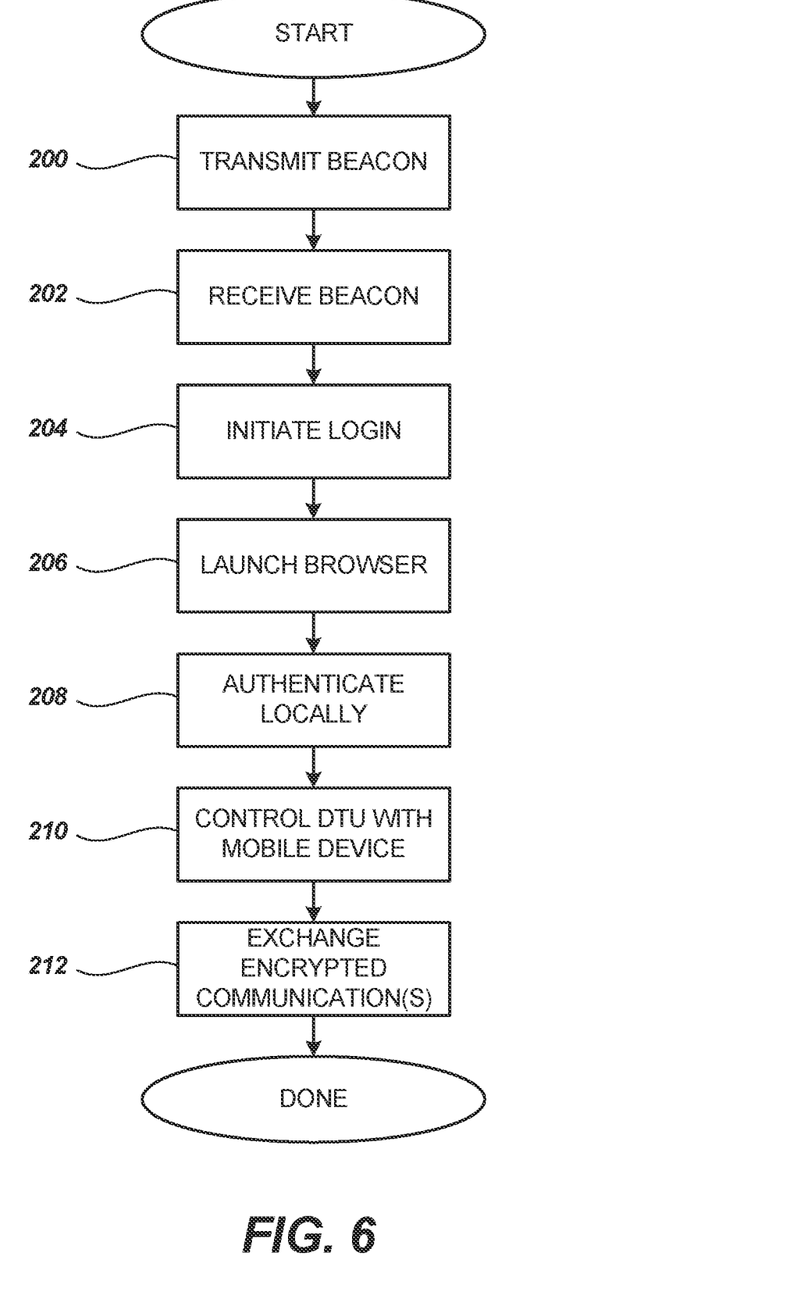
FIG. 6 is a flow chart of one embodiment of a method of device authentication for remote control and secure communication according to the present invention.

FIG. 6 is a flow chart of one embodiment of a method of authentication for the mobile computing device (or controller) 38 or 38' in the system 30 or 30'. The method illustrated in FIG. 6 is usable in conjunction with the method illustrated in FIG. 5, or in other contexts. Initially, the first wireless connection point 48A of the SV 42 can transmit a beacon, probe, or otherwise provide an indication of availability for authentication or login (step 200). Such transmission of the beacon can occur by a continuous or periodic local broadcast, so as to be receivable only within close proximity to the first wireless connection point 48A. The mobile computing device 38 or 38' can then receive the beacon (step 202), which can initiate a login or authentication protocol (step 204). The login can proceed by launching the web browser application 38B or 38B' on the mobile computing device 38 or 38' (step 206), which can include launching a new window or tab within an already-running browser application 38B or 38B' or directing such an already running browser application 38B or 38B' to a particular login resource (e.g., a browser-readable login page of the locally-served web site 46). A user can then provide login credentials via the browser application 38B or 38B', which can include a user ID and a password, for instance, and the user's mobile computing device 38 or 38' can then be locally authenticated by the SV 42 (step 208). Authentication can include exchange of certificates, keys or other security resources, in some embodiments. Authentication establishes a full communication pathway through the first wireless connection 50A, and allows the user to selectively pair the mobile computing device 38 or 38' with one or more DTUs 40 and/or 40', as well as to allow data generated or selected by the mobile computing device 38 or 38' to be recognized as acceptable for transmission to the cloud-based portal 32. It should be noted that administration of the login process can occur via the cloud-based portal 32 or via another remote computer, such as to establish user accounts and login credentials and similar administrative functions, but logins to authenticate a particular mobile computing device 38 or 38' can be conducted exclusively via the SV 42 and the locally-served web site 46. In this way, the status of the second wireless connection 50B and/or the lack of an Internet connection (e.g., network/Internet connection 36) is irrelevant to the authentication process.

After authentication, the user can control one or more selected DTUs 40 and/or 40' with the mobile computing device 38 or 38' via the user interface provided via the browser application 38B or 38B' and the locally-served web site 46 (step 210). One or more encrypted communication(s) can also be exchanged between the mobile computing device 38 or 38' and the SV 42 (step 212).

It will be recognized by those of ordinary skill in the art that the present invention provides numerous advantages and benefits. For example, the following benefits are achieved, though other benefits will be recognized in view of the entirety of the present disclosure, including the accompanying figures. Reduced size footprint and test device complexity through: (1) elimination of a need for a separate computer/laptop and replacement with suitable low cost/limited functionality processing device, such as implementing the SV with a single-board computer device (e.g., a Raspberry Pi® computing device); (2) elimination of the need for a cart to hold the DTU and related computer, though retaining ability to be used/stored on a cart; (3) elimination of the need to physically connect, disconnect and reconnect the air hose extending from the test device to each blood pressure cuff through a manifold operably connected between the DTU and test sensors (e.g., pressure cuffs). Additionally, reductions of cost and effort associated with the (a) test device, (b) software deployment and maintenance, and (c) administrative costs associated with account activation, suspension, termination, and network association are achieved. The presently-disclosed system also provides benefits in the form of improved end user productivity by reducing time-to-test through efficient login and authentication and open-ended controller compatibility, an enhanced security/encryption platform, re-allocation of the functionality of test client software so clinical and administrative reporting can be managed via a cloud portal web site associated with the cloud-based portal, bi-directional electronic data interfacing between third party client EMRs and the cloud portal website associated with the cloud-based portal, and new patient entry/origination on the cloud portal web site in addition to with the controller/SV/DTU equipment. Various benefits of these sort are achievable while allowing open-ended controller device compatibility with relatively minimal administrative burden to maintain controller device compatibility, while at the same time maintaining robust security. Moreover, relatively low hardware requirements can be maintained through unique workload distribution across multiple components of the system, and by maintaining a relatively high degree of backwards compatibility with legacy DTUs.

Any relative terms or terms of degree used herein, such as "substantially", "essentially", "generally", "approximately" and the like, should be interpreted in accordance with and subject to any applicable definitions or limits expressly stated herein. In all instances, any relative terms or terms of degree used herein should be interpreted to broadly encompass any relevant disclosed embodiments as well as such ranges or variations as would be understood by a person of ordinary skill in the art in view of the entirety of the present disclosure, such as to encompass ordinary manufacturing tolerance variations, incidental alignment variations, transitory signal/current/power fluctuations, and the like. Moreover, any relative terms or terms of degree used herein should be interpreted to encompass a range that expressly includes the designated quality, characteristic, parameter or value, without variation, as if no qualifying relative term or term of degree were utilized in the given disclosure or recitation. Furthermore, a system according to the present invention can include suitable hardware to implement software (or firmware) based teachings. Computer hardware components such as processors, memory, and the like can also be implemented as arrays of multiple components rather than as single components, unless expressly indicated otherwise.

Although the present invention has been described with reference to preferred embodiments, workers skilled in the art will recognize that changes may be made in form and detail without departing from the spirit and scope of the invention. For instance, as noted above, the SV and DTU can be integrated together in alternate embodiments. Moreover, features disclosed with respect to one embodiment can be utilized with any other embodiment.

The invention claimed is:

1. A method for using a medical system, the method comprising:

connecting a diagnostic test unit to a computer processing device, wherein the computer processing device is further linked to a client server, and wherein the client server connects to a cloud-based portal via an Internet connection;

performing a medical testing operation on a patient with the diagnostic test unit;

temporarily storing a first communication record in memory of the computer processing device, the first communication record containing medical data generated by the diagnostic test unit during the medical testing operation;

transmitting the first communication record from the computer processing device to the cloud-based portal;

erasing locally-stored data related to the first communication record from at least the computer processing device upon successful transmission of the first communication record to the cloud-based portal, wherein erasing locally-stored data occurs automatically and concurrently with a synchronization protocol that governs transmission of the first communication record to the cloud-based portal; and queuing the first communication record in the memory of the computer processing device when the Internet connection to the cloud-based portal is unavailable.

2. The method of claim 1, wherein the computer processing device is connected to the diagnostic test unit via a wireless connection.

3. A method for using a medical system, the method comprising:

connecting a diagnostic test unit to a computer processing device;

performing a medical testing operation on a patient with the diagnostic test unit;

temporarily storing a first communication record in memory of the computer processing device, the first communication record containing medical data generated by the diagnostic test unit during the medical testing operation, wherein the first communication record is configured in a portal format compatible with a secure database of a cloud-based portal;

transmitting the first communication record from the computer processing device to the cloud-based portal;

erasing locally-stored data related to the first communication record from at least the computer processing device upon successful transmission of the first communication record to the cloud-based portal, wherein erasing locally-stored data occurs automatically and concurrently with a synchronization protocol that governs transmission of the first communication record to the cloud-based portal;

obtaining additional medical data from an additional diagnostic test unit configured in a native format, wherein the native format and the portal format are different;

encapsulating the additional medical data in the portal format; and transmitting a second communication record from the computer processing device to the cloud-based portal, the second communication record comprising the additional medical data encapsulated in the portal format.

4. A medical testing and records handling system comprising:
   a mobile computing device configured to execute a web browser application, wherein the mobile computing device is further configured to generate communication records via the web browser application;
   a diagnostic test unit;
   a computer processing device that includes:
      a processor;
      memory in communication with the processor;
      an interface enabling communication between the processor and the diagnostic test unit;
      a transceiver;
      a first wireless access point generated by the transceiver providing a first wireless connection to the mobile computing device, wherein the transceiver has a local wireless transmission range;
      computer-readable instructions stored in the memory and executable by the processor providing a locally-served web site that is browser accessible over the first wireless access point, wherein the locally-served web site is adapted to receive control instructions from the web browser application of the mobile computing device over the first wireless access point and to generate command signals transmittable over the interface to the diagnostic test unit; and
      a second wireless access point operable concurrently with and independent from the first wireless access point via the transceiver;
   a client server, wherein the second wireless access point links the computer processing device to the client server; and
   a cloud-based portal in communication with the computer processing device via the client server, where cloud-based portal in communication with the client server via an Internet connection, wherein the cloud-based portal includes a secure database and serves a portal web site via at least one computer processor, and wherein the at least one computer processor serving the portal web site is located beyond the local wireless transmission range of the transceiver of the computer processing device, wherein a first of the communication records transmits data from the diagnostic test unit in a portal format compatible with the secure database of the cloud-based portal, and wherein a second of the communication records encapsulates medical data in a native format associated with an additional diagnostic test unit in the portal format, wherein the native format and the portal format are different.

5. The system of claim 4, wherein the processor transmits the command signals over a wired connection to control operation of the diagnostic test unit in response to the control instructions.

6. A medical testing and records handling system comprising:
   a mobile computing device configured to execute a web browser application, wherein the mobile computing device is further configured to generate communication records via the web browser application;
   a diagnostic test unit;
   a computer processing device that includes:
      a processor;
      memory in communication with the processor;
      an interface enabling communication between the processor and the diagnostic test unit;
      a transceiver;
      a first wireless access point generated by the transceiver providing a first wireless connection to the mobile computing device, wherein the transceiver has a local wireless transmission range;
      computer-readable instructions stored in the memory and executable by the processor providing a locally-served web site that is browser accessible over the first wireless access point, wherein the locally-served web site is adapted to receive control instructions from the web browser application of the mobile computing device over the first wireless access point and to generate command signals transmittable over the interface to the diagnostic test unit; and
      a second wireless access point operable concurrently with and independent from the first wireless access point via the transceiver,
      wherein the computer processing device further includes a queue that at least temporarily stores a first of the communication records in memory;
   a client server, wherein the second wireless access point links the computer processing device to the client server; and
   a cloud-based portal in communication with the computer processing device via the client server, where cloud-based portal in communication with the client server via an Internet connection, wherein the cloud-based portal includes a secure database and serves a portal web site via at least one computer processor, and wherein the at least one computer processor serving the portal web site is located beyond the local wireless transmission range of the transceiver of the computer processing device, and
   wherein the system is configured to purge at least the first of the communication records from the mobile computing device after transmission of the first of the communication records to the cloud-based portal.

7. A method for using a medical system, the method comprising:
   performing a medical testing operation on a patient with a diagnostic test unit that is connected to a computer processing device;
   transmitting a first communication record from the computer processing device to a cloud-based portal, the first communication record containing medical data generated by the diagnostic test unit during the medical testing operation, wherein the first communication record is configured in a portal format compatible with a secure database of the cloud-based portal;
   obtaining additional medical data from an additional diagnostic test unit configured in a native format, wherein the native format and the portal format are different;
   encapsulating the additional medical data in the portal format;

transmitting a second communication record from the computer processing device to the cloud-based portal, the second communication record comprising the additional medical data encapsulated in the portal format; and purging the first communication record from local storage on at least the computer processing device after transmission of the first communication record to the cloud-based portal.

8. The method of claim 7 and further comprising:

purging the second communication record from local storage on at least the computer processing device after transmission of the second communication record to the cloud-based portal.

\* \* \* \* \*